United States Patent [19]

Costlow et al.

[11] Patent Number: 4,788,302

[45] Date of Patent: Nov. 29, 1988

[54] ANTI-FOULING COMPOUND AND METHOD OF USE

[75] Inventors: John D. Costlow; Irving R. Hooper; Daniel Rittschof, all of Beaufort, N.C.

[73] Assignee: Duke University, Durham, N.C.

[21] Appl. No.: 824,959

[22] Filed: Jan. 31, 1986

Related U.S. Application Data

[63] Continuation-in-part of Ser. No. 744,523, Jun. 14, 1985, abandoned.

[51] Int. Cl.$^4$ .................. C07D 307/92; A61K 31/34; C09D 5/14
[52] U.S. Cl. ..................................... 549/458; 514/468; 106/15.05
[58] Field of Search ......................... 424/95; 106/15.5; 428/514; 549/458; 514/468

[56] References Cited

PUBLICATIONS

Chem. Abst. 99:1195742, 1983.

Primary Examiner—John Rollins
Attorney, Agent, or Firm—Oblon, Fisher, Spivak, McClelland & Maier

[57] ABSTRACT

A tissue extract containing a low molecular weight, non-proteinaceous compound selected from the group consisting of (A) methanol-soluble compounds obtainable from *Leptogorgia virgulata* with $R_f$ values in reverse-phase, thin layer, silica gel chromatography of (1) 0.42, 0.54, and 0.62; (2) 0.35, 0.50, and 0.58; (3) 0.37, 0.47, and 0.58; or (4) 0.31, 0.43, and 0.54, respectively, in 1:1:1 methanol:ethyl acetate:water, 2:1:1 methanol:ethyl acetate:water, and 1:2:1 methanol:ethyl acetate:water, or (B) methanol-soluble compounds obtainable from *Renilla reinformis* with $R_f$ values in thin layer, silica gel chromatography of (1) 0:44, 0.37, and 0.53; (2) 0.52, 0.42, and 0.60; (3) 0.56, 0.43, and 0.63; or (4) 0.32, 0.26, and 0.37, respectively, in 9:1 chloroform:acetonitrile, 9:1 methylene chloride:acetonitrile, and 4:1 methylene chloride:acetonitrile and compositions containing the same, which is useful as antifouling compositions, is disclosed.

7 Claims, 8 Drawing Sheets

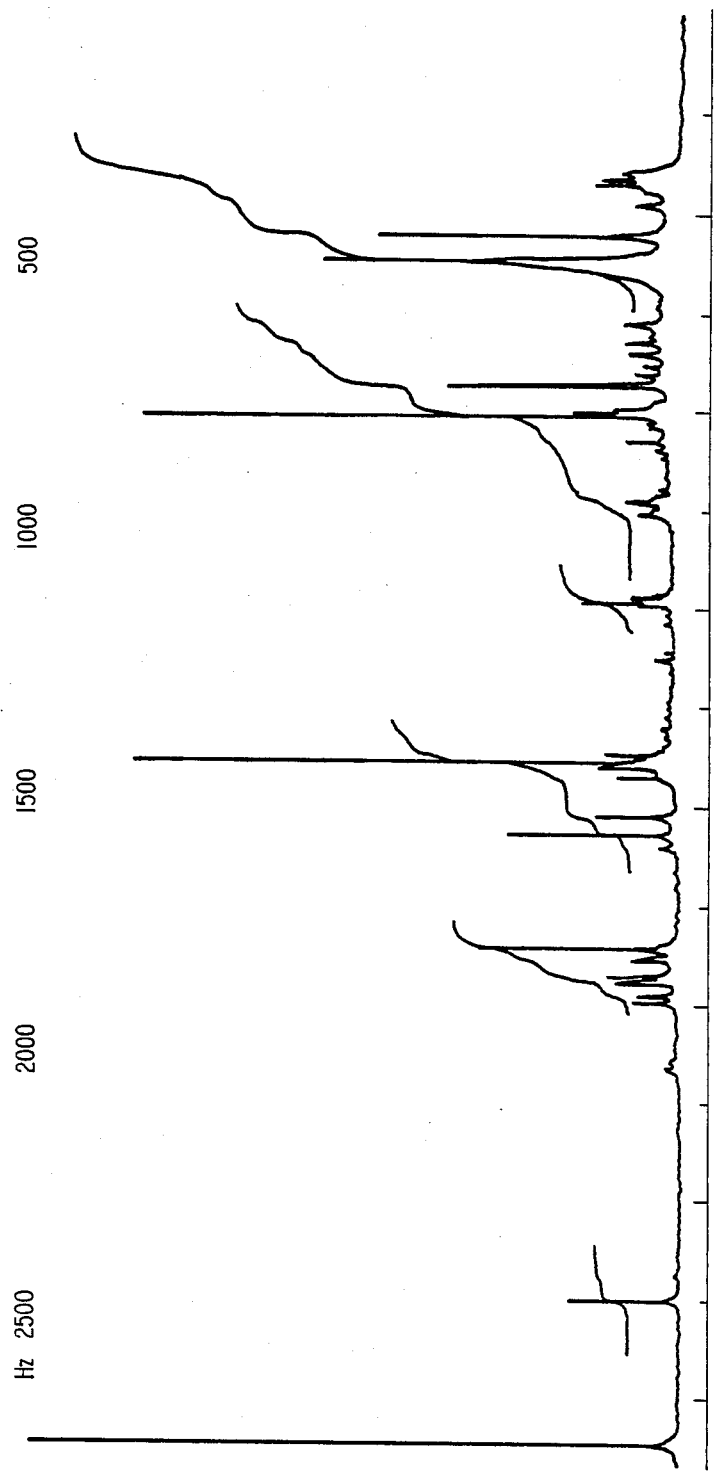
FIG. 5A PROTON NUCLEAR MAGNETIC RESONANCE OF LVI

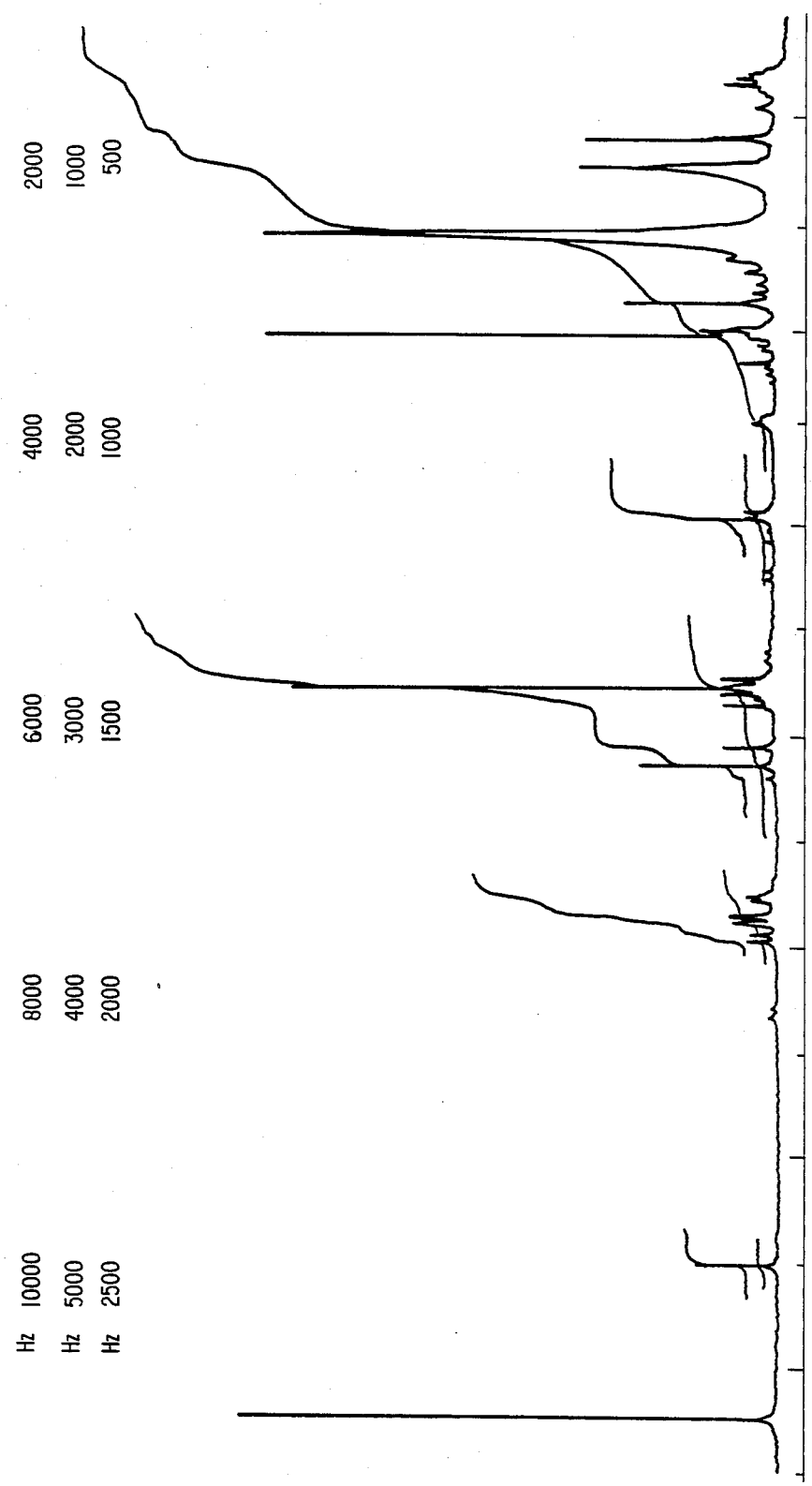
FIG. 5B PROTON NUCLEAR MAGNETIC RESONANCE OF LVII

ANTI-FOULING COMPOUND AND METHOD OF USE

This application is a continuation-in-part of application Ser. No. 744,523 filed June 14, 1985, now abandoned.

BACKGROUND OF THE INVENTION

Studies leading to the present invention were supported in part by funding from the Office of Naval Research, and the United States Government has rights in this invention as a result thereof.

1. Field of the Invention

This invention relates to compositions obtained from natural sources useful for the treatment of submerged surfaces, such as marine or other aquatic structures of ship hulls, in order to prevent fouling of the surfaces by aquatic organisms.

2. Background Information

It is well-known that the growth of organisms (micro- or macro-fouling matters) on the submerged parts of a structure may have detrimental effects on their operation and their corrosion rate. For example, in the techniques of oil production at sea, the fouling may accelerate the corrosion of submerged structures such as supports of drilling platforms. The weight increase resulting from the deposit of the fouling matter also results in difficulties when raising up certain submerged structures, as it is the case for the pipe-lines used to collect oil at sea; it also requires frequent operations for the maintenance of the floats of signal or meterologic buoys. On the other hand, the formation of even a very thin layer of microfouling is sufficient to reduce the transmission of light and sound and consequently to disturb the operation of certain devices such as sonar sea-marks. The fouling matter may also be a medium favorable to the proliferation of certain microorganisms responsible for the biodegradation of organic materials and of concrete. It is also known that the cooling systems for plants and power stations, either of the nuclear or of the conventional type, that are operated with sea water are also subject to severe fouling which may plug ducts and condensors. Finally, fouling by large organisms such as the balani, the serpulae and the algae, increases the roughness of the hull of ships and their drag in water, thereby resulting in an increase of fuel consumption and/or a reduction of the ship speed. These various problems and their consequences emphasize the importance of anti-fouling substances.

Besides the periodic cleaning of the surfaces or the use of paints enabling a controlled exfoliation, which are very expensive remedies, the principle of most anti-fouling action is to create a toxic zone on the surfaces to be protected. For example, chlorine is used successfully in a continuous manner in sea water ducts, but this technique is obviously unsatisfactory as far as the preservation of the natural environment is concerned.

An efficient way of combating fouling must (by prior art) comprise the maintenance of the toxic product at an efficient and homogeneous concentration and in a continuous manner on the whole surface. This is the reason why the so-called "anti-fouling" paints have taken an important place among the anti-fouling means. Thus, in order to fight against the growth of sea organisms on submerged surfaces and hulls of boats, an anti-fouling paint is generally applied as an upper layer. According to the known techniques, this antifouling paint contains a toxic substance which slowly reacts with sea-water to give a salt soluble in water and which is lixiviated from the paint pellicle. Among the toxic substances which are the most commonly used, there can be mentioned cuprous oxide, tin tri-n-butyl oxide, tin tri-n-butyl fluoride and tin tri-n-butyl sulfide, these compounds being biocidic agents with activity against a wide range of a sea organisms.

However, these organo-metallic compounds are general toxicants and have adverse effects on all types of sea life, their action not being limited to the inhibition of marine fouling. More specific anti-fouling compositions are therefore desirable. For example, it was known that various marine organisms apparently were resistant to fouling of various types. It was unlikely that a general toxicant was excreted by such marine organisms because of the abundance of marine life in the vicinity of such organisms, such as corals. However, isolation and identification of the active compounds in marine corals had not taken place prior to the present invention. Accordingly, there remained a need for substances of biological origin that exhibit less toxicity when used as antifouling agents than those materials that were previously used.

SUMMARY OF THE INVENTION

Accordingly, it is an object of the present invention to provide a method of preventing fouling of aquatic surfaces by organisms which does not contaminate the environment to the extent that contamination occurred using previous anti-fouling methods.

This and other objects of the invention as will hereinafter become more readily apparent have been accomplished by providing a composition capable of inhibiting barnacle settlement which contains a low molecular weight, non-proteinaceous compound selected from the group consisting of (A) methanol-soluble compounds obtainable from *Leptogorgia virgulata* with $R_F$ values in reverse-phase, thin layer, silica gel chromatography of (1) 0.42, 0.54, and 0.62; (2) 0.35, 0.50, and 0.58; (3) 0.37, 0.47, and 0.58; or (4) 0.31, 0.43, and 0.54, respectively, in 1:1:1 methanol:ethyl acetate:water, 2:1:1 methanol:ethyl acetate:water, and 1:2:1 methanol:ethyl acetate:water, or (B) methanolsoluble compounds obtainable from *Renilla reniformis* with $R_F$ values in thin layer, silica gel chromatography of (1) 0.44, 0.37, and 0.53; (2) 0.52, 0.42, and 0.60; (3) 0.56, 0.43, and 0.63; or (4) 0.32, 0.26, and 0.37, respectively, in 9:1 chloroform:acetonitrile, 9:1 methylene chloride:acetonitrile, and 4:1 methylene chloride:acetonitrile. The structures of three compounds have been identified as shown below:

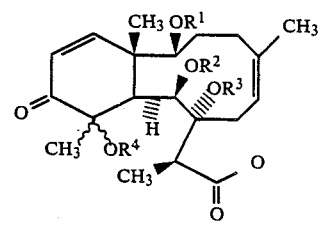

in which (1) $R^1 = R^2 =$ acetate, $R^3 = R^4 = H$; (2) $R^1$ and $R^2$ alternately represent acetate and propionate, $R^3 = R^4 = H$; and (3) $R^1$ and $R^2$ alternately represent acetate and butyrate, $R^3 = R^4 = H$. Other compounds having the same type of biological activity can be prepared by replacing R¹ and R² with other alkanoyls or by replacing the H at R³ or R⁴ with an alkanoyl.

BRIEF DESCRIPTION OF THE DRAWINGS

A more complete appreciation of the invention will readily be obtained by reference to the following detailed description when considered in connection with the accompanying drawings, wherein:

FIG. 5 (A and B) shows proton magnetic resonance spectra of inhibitor fractions LVI and LVII from *L. virgulata*.

DESCRIPTION OF THE PREFERRED EMBODIMENTS

Figure 1:
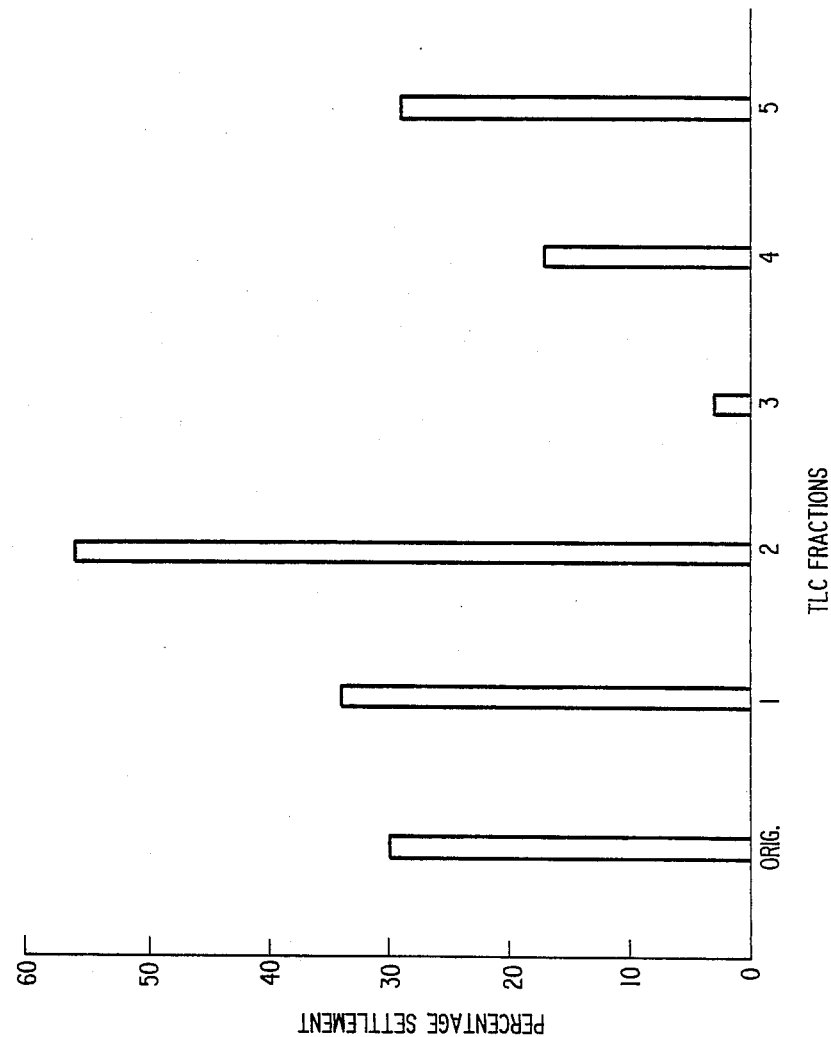
FIG. 1 is a graph showing a settlement assay of TLC-fractionated methylene chloride extract of sea pansy. Test shown is response of barnacle larvae in settlement assay to 6.25 mg original ml$^{-1}$. Zone 2 (rf of 0.2 to 0.35) significantly facilitated settlement at this concentration. Zone 3 (rf of 0.35 - 0.56) contained potent inhibitor activities. The other zones were weakly active at best.

The present invention arose in part from studies indicating that several low-molecular weight compounds extractable from *Leptogorgia virgulata* and *Renilla reniformis* are capable of acting as inhibitors of barnacle settlement. Experimental studies have demonstrated that the inhibitory materials prevent or retard settlement of barnacle cyprids at low concentrations. Accordingly, the inhibitory materials can be used in preventing barnacle settlement by applying the inhibitor to surfaces in contact with sea water or by releasing low levels of the inhibitor into the water surrounding an object desired to be protected from barnacle attachment.

The settling inhibitors can be prepared from tissue samples of *Leptogorgia virgulata* and *Renilla reniformis* by mixing the samples together with water and homogenizing the samples in a blender (or by other processes that result in cell disruption). Organic solvents can be used to extract low molecular weight materials (less than 1000 daltons) having inhibitory activity. These materials can be used in any manner in which other inhibitors of barnacle settlement can be used, such as in anti-fouling paints. Specific examples of use are set forth in this specification at a later time.

Typically, compositions of the invention can be prepared from either fresh or frozen tissues of *Leptogorgia virgulata*. The tissue samples are mixed with water, preferably in an approximately 1:1 w/v ratio prior to homogenization. Homogenization is carried out by any method that will result in disruption of the tissues and cells, such as crushing or shearing, typically in a blender. Homogenized soft tissues are centrifuged at approximately 6000 xg, preferably for about 10 minutes, to separate a supernatant from tissue and shell fragments. The supernatant contains the inhibitor. Water is removed from the supernatant, preferably by lyophilization, and the solids are suspended in approximately 1/10 the original amount of water. The resuspended solids are dialyzed against two changes of approximately 10-fold excesses of water using a dialysis medium with a molecular weight cut-off of no less than approximately 10,000. Water is again removed from the dialyzate, and the solids are mixed with 100% methanol. After centrifugation at approximately 10,000 g, for approximately 10 minutes, a clear yellow solution containing the low molecular weight inhibitor is obtained. This fraction may be used as an inhibitor, or further purification can be carried out if desired.

Extracts of *Renilla reniformis* can be prepared in the same manner, although minor modifications give somewhat better yields. For example, homogenization is typically carried out and 1:3 w:v water. After homogenization, particulate matter is removed by settling and decantation. The supernatant is centrifuged at approximately 7000 xg, preferably for about 10 minutes, and the pellet is discarded. Water is removed from the supernatant, preferably by lyophilization, and the solids are suspended in 100% methanol. The slurry is clarified by centrifugation for approximately 10 minutes at about 5000 xg to give a crude extract containing the methanol-soluble compounds of the invention. This fraction may also be used as an inhibitor (optionally after drying or resuspension in another solvent), or further purification can be carried out if desired.

Standard chromotagraphy techniques can be used to isolate individual compounds of the invention, using the specific techniques set forth in the following examples. The particular separation techniques described are by known means unique, and other means of isolating the compounds of the invention can readily be determined by simple experimentation. However, it is possible to reproducibly obtain individual compounds of the invention by following the techniques set forth in the following examples.

Nine individual compounds have been identified, and characterization of these compounds has begun, although characterization is not yet fully complete. Nevertheless, since the compounds have been isolated as individual compounds, it is contemplated that all structures of these compounds can readily be assigned from the purified compounds now available. Structures of three compounds have been determined and are set forth below.

The compounds of the invention appear to be low molecular weight, non-proteinaceous compounds containing carbon, hydrogen, and possibly oxygen, but no nitrogen. The molecular weights of four compounds have been specifically identified; two have a molecular weight of 478 and two more have a molecular weight of 492. The molecular formula of one compound, having a molecular weight of 492, has been identified as $C_{26}H_{36}O_9$. Identifying chromatography characteristics, molecular weights, and molecular formulas (where known) are set forth in Table 1 below.

TABLE 1

| Compound | Compounds from *L. virgulata* TLC Data ($R_f$ values)[1] | | |
| --- | --- | --- | --- |
| | MeOH:ETOAc:H$_2$O 1:1:1 | MeOH:ETOAc:H$_2$O 2:1:1 | MeOH:ETOAc:H$_2$O 1:2:1 |
| LVIa | 0.42 | 0.54 | 0.62 |
| LVIb | 0.35 | 0.50 | 0.58 |
| LVIIa | 0.37 | 0.47 | 0.58 |
| LVIIb | 0.31 | 0.43 | 0.54 |

| Compound | Compounds from *R. reniformis* TLC Data ($R_f$ values)[1] | | |
| --- | --- | --- | --- |
| | CHCl$_3$:acetonitrile 9:1 | CH$_2$Cl$_2$:acetonitrile 9:1 | CH$_2$Cl$_2$:acetonitrile 4:1 |
| RRI | 0.44 | 0.37 | 0.53 |
| RRII[2] | 0.52 | 0.42 | 0.60 |
| RRIII[3] | 0.56 | 0.43 | 0.63 |
| RRIV[4,5] | 0.32 | 0.26 | 0.37 |

[1] Refer to the following Examples for details of TLC analysis.
[2] RRII has a molecular weight of 478.
[3] RRIII has a molecular weight of 492 and a molecular formula of C$_{26}$H$_{36}$O$_9$.
[4] RRIV is a mixture of two distinct compounds (a and b) with molecular weights of 478 and 492, respectively.
[5] Compounds RRI - RRIV can be identified in the Examples section by their relative mobilities in normal and reverse-phase silica gel chromatography as follows: RRI = silica fast band of activity, reverse-phase fast band of activity; RRII '2 silica fast, reverse-phase medium; RRIII = silica fast, reverse-phase slow; and RRIV = silica slow, reverse-phase slow.

Figure 6A:
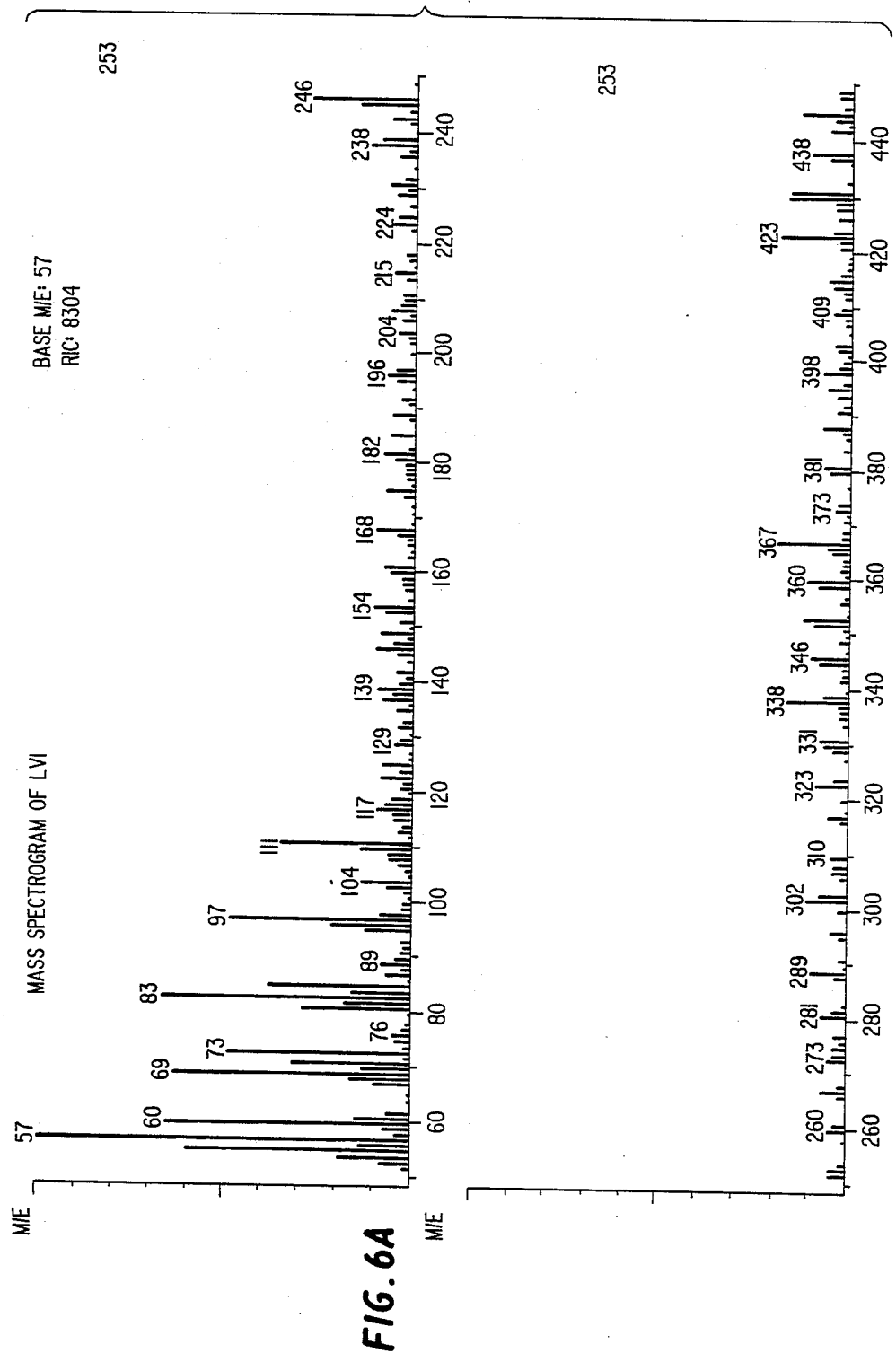
FIG. 6 (A and B) shows mass spectra of inhibitor fractions LVI and LVII from *L. virgulata*.
Figure 6B:
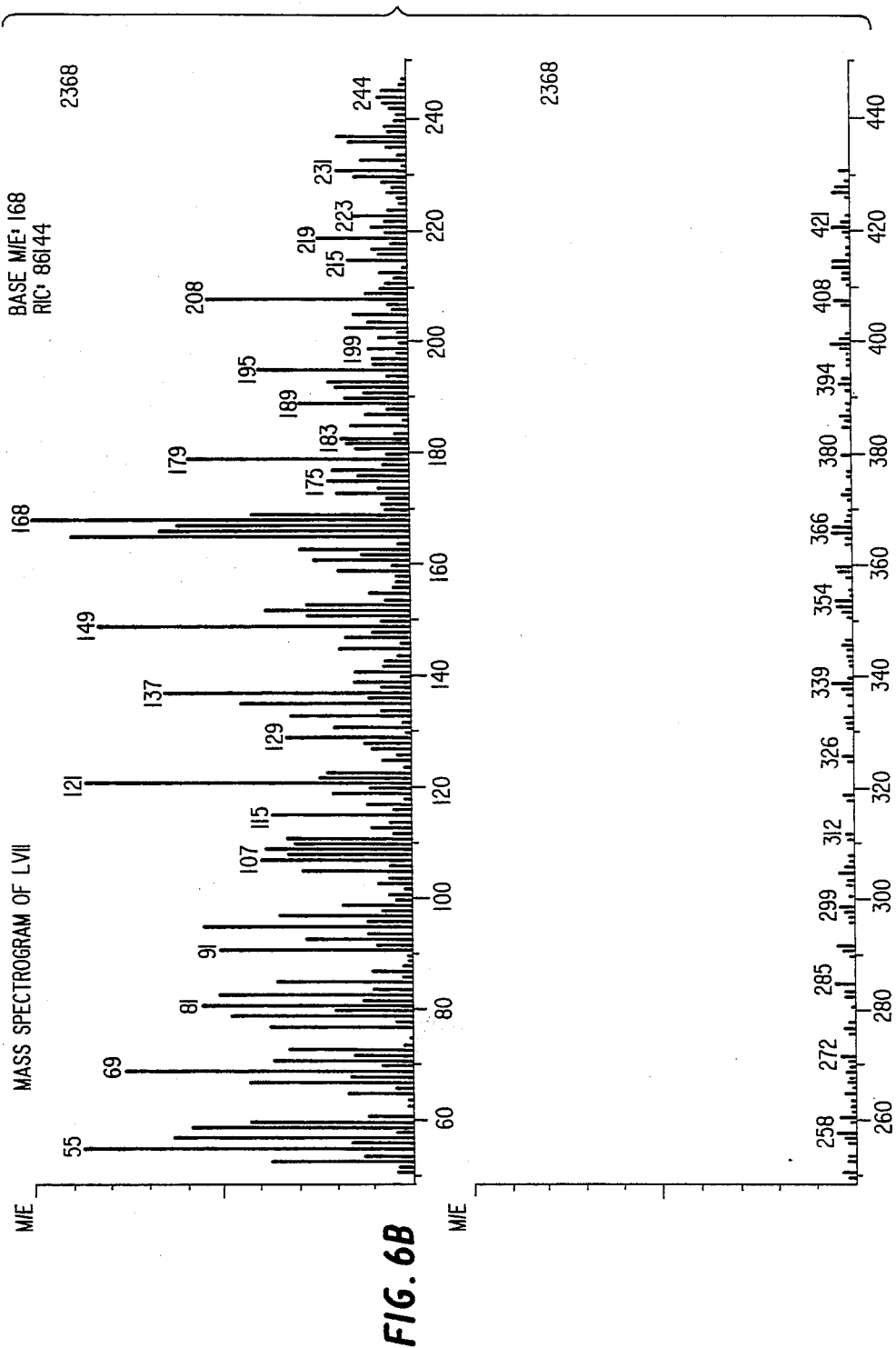

Additionally, mass spectographic and proton nuclear magnetic resonance data is available for some compounds of the invention. This data is set forth in standard graphical form in FIGS. 5 and 6. This data was obtained on a mixture of compounds LVIa and LVIb (referred to in the Figures as LVI) and a mixture of LVIIa and LVIIb (referred to in the Figures as LVII).

Three novel structures have been identified as set forth below:

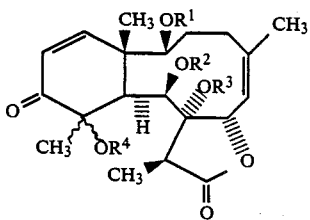

Compound RRI: $R^1=R^2$=acetate; $R^3=R^4$=H

Compound RRII: $R^1$ and $R^2$=acetate and propionate; $R^3=R^4$=H

Compound RRIII: $R^1$ and $R^2$=acetate and butyrate; $R^3=R^4$=H

The specific locations of the two alkanoyl substituents in RRII and RRIII have not been determined. Thus in RRII, $R^1$ or $R^2$ is an acetate and the remaining group is a propionate. A similar situation exists for RRII.

The various alkanoyls present in the compounds shown above do not appear to have any significant effect on anti-settlement activity. Thus, it appears that $R^1$, $R^2$, $R^3$, and $R^4$ can independently represent either H or a C$_{1-18}$ alkanoyl or alkenoyl group. Preferred are alkanoyl groups containing up to 12 carbons, more preferably up to 6 carbons. A total of 36 or fewer carbons in the various alkanoyl and/or alkenoyl substituents is preferred, more preferably 24 or fewer, most preferably 12 or fewer. Compounds in which $R^3=R^4$=H are preferred. Specifically preferred alkanoyl groups for $R^1$ and $R^2$ are acetate, propionate, and butyrate.

Compounds having a different acyl substitution pattern from the specific compounds shown can readily be prepared from the isolated compounds described alone by an acyl exchange reaction using standard techniques (i.e., an ester exchange reaction or an esterfication reaction). Because of the ease with which mixtures can be synthesized, mixtures are preferred for use in anti-foulant compositions. However, as is indicated by the discussion above and the Examples which follow, compounds having different alkanoyl groups can readily be separated by thin-layer chromatography.

Compounds identified as LVII and LVIIb in this specification have been determined to be identical to the previously known compounds pukalide and pukalide epoxide. Thus, these compounds are excluded from claimed compounds. However, neither of these compounds was known to have anti-fouling properties so that claims to a method of preventing fouling include the use of these compounds as do claims directed to anti-fouling compositions.

Compounds of the invention as well as tissue extracts containing these compounds can be used to prevent the settlement of barnacles by applying a composition containing a compound of the invention to an aquatic surface. The amount of material needed to measurably inhibit barnacle settlement can readily be determined by simple experimentation and will naturally vary with the compound selected and the concentration of that compound in the composition used. It is also possible to inhibit barnacle settlement by releasing a compound of the invention into the aquatic environment surrounding a surface on which settlement is to be inhibited. Guidelines for determining the amount of inhibitory material are present in the following examples. The compounds are extremely potent and are effective when present in inhibiting concentrations of significantly less than 1 mg/ml. Inhibitory activity at 0.05 ug/ml has been detected. No upper limit on the effective concentration is apparent.

Compositions containing compounds of the invention that can be used in the inhibition of barnacle settlement are not known to be limited by any other component that may be present in the composition. Since active compounds are soluble in methanol and other organic solvents, such as methylene chloride, solutions prepared in organic solvents represent preferred compositions for use in applying compounds of the invention to aquatic surfaces. Solutions having concentrations from the saturation level down to onetenth the saturation level are preferred. It is also possible to prepare compositions of the invention in the form of anti-fouling paint compositions using paint formulations now used to apply toxic materials such as the organic-tin compounds described in the Background of the Invention section of this specification. These paints can be modified simply by replacing the organometallic component with one or more compounds of the invention. It is also possible to use unpurified tissue extracts as described herein in such paint compositions. The formulation of paints containing materials soluble in organic solvents is a known process and need not be described here in detail. Paint compositions containing up to 10% of an organic solution of one or more compounds of the invention are preferred. Lower limits have been previously described. Higher limits are possible but may adversely effect the properties of the paint.

The invention now being generally described, the same will be understood by reference to specific examples which are included for purposes of illustration only and are not intended to be limiting of the invention unless otherwise specified.

EXAMPLE

CULTURE OF LARVAL BARNACLES FOR SETTLEMENT ASSAYS

*Balanus amphitrite* cyprids were cultured from stage 1 nauplii as described by Rittschof et al., *J. Exp. Mar. Biol. Ecol.* 82:131–146 (1984). The day of metamorphosis to cyprid was called day 0. Cyprids were stored in the dark at 4° C. until the day of use.

BIOLOGICAL ASSAYS

Behavior Assay

Behavior assays were performed as described by Rittschof (Rittschof et al., (1984)). Briefly, a 120 cm x 3.7 mm i.d. Pyrex tube was used as an assay chamber. A low (15-17%) level of larval attaching behavior was promoted by coating chambers with a 5-sec rinse of a 250 ng protein ml$^{-1}$ solution of settlement factor derived from *Balanus amphitrite* homogenate (Lahrman et al., *Comp. biochem. and Physiol.*, 72B:329-338 (1982); Rittschof et al., (1984)). A high level of attaching behavior (50-70%) was promoted by coating the chamber with a $\mu$g protein ml$^{-1}$ solution of settlement factor. In uncoated tubes 5-7% of cyprids exhibited sticking behavior. Cyprids were placed in the upstream 10 cm of the tube and flow generating a velocity gradient (Crisp, *J. Exp. Biol.* 32:569-590 (1955)) of 39 sec$^{-1}$ was initiated. Flow was stopped after 10 min, and the tube was drained at a velocity gradient of 606 sec$^{-1}$. Cyprids remaining in the tube were scored as stickers; those flushed from the tube upon draining were counted as sliders. Cyprids that passed through the tube in the first 10 min were scored as swimmers.

Settlement Assay

In settlement assays 25-50 3-day-old cyprids/replicate were incubated for 20 h at 25° C. and a 15:9 light-dark light regime (11 L:9 D in tests) in covered polystyrene petri dishes (Falcon #1006, Rittschof et al., (1984)). Test compounds were added to filtered seawater (<100,000 Daltons). The residue from a water sample taken through the fractionation procedure was run as a control. Experimental solutions were made by dissolving vacuum-dried test samples in 100,000-Dalton filtered seawater. From two to seven concentrations of test solution, each with 3 to 6 replicates, were tested by comparing frequency of permanent attachment (shown as percentage settlement) in experimental solutions to attachment in the controls.

Preparation of Assay Samples

Assays testing effects of solvents showed that cyprid settlement was inhibited by small amounts (1 )1 methanol ml$^{-1}$ for example) of organic solvents. Therefore, samples for bioassay were dried under vacuum to remove solvents. After drying, samples were diluted in seawater with concentrations expressed as mg original animal homogenized ml$^{-1}$ seawater. Experiments testing the inhibitory effects of solvents dried in the same fashion showed drying eliminated interference caused by solvents.

Reagents and Supplies

Solvents were reagent grade or purer. Methanol was HPLC grade from Fisher;, methylene chloride and chloroform were reagent grade from Fisher Scientific. Methylene chloride was redistilled prior to use. Analytical thin layer plates (microscope slide size) were: (1) silica with indicator (Whatman #MK6F); (2) reverse phase silica with indicator (Whatman #MKC18F). Preparative silica TLC plates with indicator were Whatman #PK6F. Reverse phase Sep-Pak$^R$ cartridges were from Waters Corporation.

Fractionation of *L. virgulata*

Fresh or frozen tissue samples (300 to 700 g) were mixed 1:1 w/v with water purified by reverse-osmosis (R-0) and homogenized for 2 min in a seven-speed Waring Blender at a setting of 7. Axial skeleton settled out. Homogenized soft tissues were decanted into centrifuge bottles and centrifuged at 6000 x g for 10 minutes. The supernate was transferred immediately to lyophilization flasks, shell-frozen, and lyophilized. Solids were resuspended in 50-75 ml R-0 water and dialyzed against two 500 to 750 ml changes of water. The dialysate was lyophilized, and the solids were mixed with 100% methanol and centrifuged at 10,000 x g for 10 min. The supernate, a clear yellow solution, was termed the low molecular weight fraction (LMW).

Sep-Pak$^R$ Fractions

Sep-Pak$^R$ C18 Cartridges (low pressure chromatography columns made by Waters Assoc. in Milford, Mass.) were conditioned by washing at 1 ml min$^{-1}$ min with at least 20 ml of 100% methanol. Cartridges were equilibrated to application conditions prior to application of material to be fractionated. Material was applied to the cartridges at a flow of 1 ml min$^{-1}$. Capacity experiments showed that substantial leakage of active material could be expected if the equivalent of more than 40 grams of original homogenate was applied to a cartridge. After application the cartridge was washed with 10 ml of application solvent and then eluted with 10 ml volumes of increasing concentrations of methanol in R-0 water. Eluates were concentrated to near dryness by rotary evaporation.

Solvent Extraction

Preparation of inhibitor was simplified once inhibitory substances were detected by their characteristic migration in two TLC systems. After homogenization, centrifugation and lyophilization, material was resuspended in 100% methanol at a concentration of 2 to 6 g of original ml$^{-1}$, and the resultant slurry was centrifuged at 10,000 x g for 10 min. The clear yellow supernate was diluted to 25-40% methanol with water, filtered to remove a cloudy precipitate, and extracted with 3 x ¼ vol of methylene chloride. The solvent extract was evaporated to dryness under vacuum, redissolved in a small amount of methanol or methanol-methylene chloride (100 g of original ml$^{-1}$). This material was used in preparative scale purifications.

Procedures for Scale Isolation of Inhibitors from *L. virgulata*

Solvent extract was applied to preparative TLC plates in 0.5 x 20 cm band at the origin. Plates were developed with 95:5 chloroform:methanol and zones made visible by quenching of short wave UV fluorescence. Zones were scraped off plates and eluted with small volumes of methanol.

Preparation of Inhibitor from Renilla reniformis

An aqueous extract of whole soft coral was prepared by homogenization 1:3 w:v in reverse-osmosis (R-0) water. Homogenization was for 3 min in a Waring Blender on the highest setting. After homogenization, particulate material was allowed three minutes to settle, and the solution was decanted into 250 ml centrifuge bottles and centrifuged for 10 min at 7000 x g at 4° C. Pellets were discarded. Supernates were combined, shell frozen and lyophilized to dryness. Dried material was resuspended in 100% methanol at a concentration of 2 g of original wet weight of animal per ml. This slurry was clarified by centrifugation for 10 min at 5000 x g. Pellets were discarded and the supernates combined. The inhibitor preparation at this level of purification is termed the Crude Inhibitor Preparation.

Methylene Chloride Extraction

Crude Inhibitor Preparation was diluted 1:3 v:v with R-0 water and filtered with filter aid (FEMCO grade V-30R Filtermedia Co., Houston, Tex., U.S.A.). The slightly cloudy light-yellow solution was extracted three times with 0.2:1 volumes of methylene chloride. The methylene chloride was filtered through Watman #1 paper to remove aqueous dispersions and evaporated to dryness. The yellow residue was redissolved in methanol or methanol/methylene chloride at a concentration of 200 g of whole animal weight/ml. This material is termed the Methylene Chloride Extract.

Thin Layer Chromatography on Silica

Methylene Chloride Extract was fractionated by preparative TLC on silica. The equivalent of 100–200 g of original was applied to an 20 cm x 20 cm Whatman preparative silica plate with fluorescent indicator. Development was with 9:1 methylene chloride:acetonitrile. Short-wave UV was used to partition the plate into three regions containing fluorescence quenching material and two that did not. Material was recovered from each region by scraping the region and eluting with 100% methanol.

Reversed Phase TLC Fractionation of Settlement Inhibitors

Analytical reverse-phase TLC was used to determine separation conditions for preparative scale purification of the fractions containing settlement inhibitor from preparative scale straight phase TLC. A variety of solvent mixtures effective in separating settlement inhibitors from *Leptogorgia virgulata* (Rittschof et al. *J. Chem. Ecol.* 11:551–563 (1985)) were tested. The most effective system was acetonitrile:water 2:1 although in some earlier work 3:1 mixtures were used. Preparative plates were run with material equivalent to 100–300 g of original animal per 20 x 20 cm plate.

EXPERIMENTS

The experiments:

1. confirm the existence of low molecular weight natural products from soft corals that function as settlement inhibitors for barnacle larvae and for bryozoan larvae.
2. characterize the settlement inhibition as acting by molecules adsorbing to surfaces
3. show ways to chemically isolate and characterize settlement inhibitor.

Activities in the LMW fraction of *L. virgulata*

Behavior Inhibition

The low molecular weight fraction of *L. virgulata* was tested for behavior effects (Table 2). Assay tubes were rinsed in a 250 ng protein $ml^{-1}$ solution of settlement factor to promote a low level of sticking behavior. Test substances were dissolved in seawater and were passed through the tubes at a flow rate of 7.5 $ml^{-1}$ min. Cyprids in the control assay (without addition to seawater) responded to flow and surface reproducibly and in high percentage (72%) by swimming. Smaller percentages of cyprids (13%) slid down the tube or actively attached (15%) by their antennae (stickers). When not swimming, cyprids retracted their thoracic appendages. Exposed to a concentration of 20 mg original $ml^{-1}$ of LMW most cyprids (88%) slid down the tube. As compared to control there was a significantly reduced frequency of swimmers and stickers and a significantl increased frequency of sliders (Table 1). Cyprids appeared to be immobilized and did not completely retract their thoracic appendages when not swimming. Tests with a concentration of 5 mg original $ml^{-1}$ gave results intermediate to control and 20 mg original $ml^{-1}$ and significantly different from both (overall $G=261.92$ $p<0.005$). Cyprids in 5 mg $ml^{-1}$ appeared normal upon microscopic investigation, but responded significantly less by swimming and sticking and significantly more by sliding than controls (Table 2). In some preparations inhibitory activity (increased sliding) was observed at concentrations of 0.5 mg original $ml^{-1}$.

TABLE 2

Modification of larvae behavior by LMW.

| | Control 1 | Control 2 | LMW 20 $mg/ml^{-1}$ | LMW 5 $mg/ml^{-1}$ |
|---|---|---|---|---|
| n | 335 | 290 | 345 | 482 |
| Behavior | % Total | % Total | % Total | % Total |
| Swimmers | 72 | 72 | 12 | 60 |
| Sliders | 13 | 13 | 88 | 34 |
| Stickers | 15 | 15 | 0 | 5 |

Settlement Inhibition by Extracts of L. virgulata

Settlement assays were used to test for settlement inhibition activity in the LMW fraction. LMW significantly inhibited settlement at concentrations of 20 and 10 mg original ml$^{-1}$ and was ineffective at 5 mg ml$^{-1}$ (Table 3). Although some variability in inhibitory activity between L. virgulata LMW preparations was observed, inhibitory activity was always observed at a concentration between 2 and 10 mg of original ml$^{-1}$.

TABLE 3

| Inhibition of barnacle settlement by LMW[S]. | | | | | |
|---|---|---|---|---|---|
| Treatment | Set | Not Set | % Set | G* | P |
| Control | 63 | 92 | 41 | — | — |
| 20 mg/ml$^{-1}$ | 26 | 118 | 18 | 17.56 | <.001 |
| 10 mg/ml$^{-1}$ | 39 | 109 | 26 | 6.34 | <.010 |
| 5 mg/ml$^{-1}$ | 75 | 115 | 39 | 0.01 | ns |

*Statistical comparisons are to control.
[S]EC$_{50}$ = 16.608 mg/ml$^{-1}$ (95% confidence interval 26.3–12.5)

Behavior Inhibition by Extracts of L. virgulata

LMW fraction was applied to a C$_{18}$ Sep-Pak$^R$ in water, washed with water and eluted with 80% methanol. The effluent and 80% methanol eluate were tested for behavior and settlement inhibition activity. Tests of the Sep-Pak$^R$ effluent and the 80% methanol eluate of adsorbed material showed that behavior inhibitor was not adsorbed on the cartridge (Table 4). As reported in the case of the LMW, the aqueous effluent caused significant increase in the numbers of sliders and significant decreases in the numbers of swimmers and stickers. The 80% methanol eluate had no effect on behavior at the same relative concentration. Behavioral responses to the 80% eluate were not significantly different from the control, but were significantly different from the effluent (overall G=122.07 p<0.005).

TABLE 4

| Location of behavior inhibition in Sep-Pak ® fractions. | | | |
|---|---|---|---|
| | Control 1 | Sep-Pak ® Effluent | Sep-Pak ® Eluate |
| n | 875 | 677 | 539 |
| Behavior | % Total | % Total | % Total |
| Swimmers | 28 | 9 | 24 |
| Sliders | 20 | 53 | 24 |
| Stickers | 52 | 38 | 52 |

Settlement Inhibition by Fractions of L. virgulata Extracts

Sep-Pak Fraction Sep-Pak$^R$ effluent and 80% methanol eluate of LMW were tested in settlement assays to determine location of settlement inhibition activity (Table 5). There was no detectable inhibition of settlement by the effluent at 32 mg original ml$^{-1}$. Effluent at 8 mg ml$^{-1}$ significantly increased settlement over control. The 80% methanol eluate significantly inhibited settlement at concentrations of 16, 8, 4 and 2 mg original ml$^{-1}$.

TABLE 5

| Settlement inhibition by Sep-Pak ® fractionated LMW. | | | | | |
|---|---|---|---|---|---|
| Treatment | Set | Not Set | % Set | G* | P |
| Control | 70 | 116 | 38 | — | — |
| Effluent | | | | | |
| 32 mg/ml$^{-1}$ | 155 | 276 | 36 | 00.09 | ns |
| 8 mg/ml$^{-1}$ | 160 | 174 | 48 | 04.73 | <.050 |
| 80% Methanol Eluate | | | | | |
| 16 mg/ml$^{-1}$ | 3 | 232 | 01 | 106.87 | <.001 |
| 8 mg/ml$^{-1}$ | 1 | 200 | 01 | 105.36 | <.001 |
| 4 mg/ml$^{-1}$ | 14 | 234 | 06 | 70.15 | <.001 |
| 2 mg/ml$^{-1}$ | 22 | 240 | 08 | 55.61 | <.001 |

*Comparisons are made to the control.
EC$_{50}$ = 0.600 mg/ml$^{-1}$ (95% confidence limits 1.13–0.12 mg/ml$^{-1}$)

Tests were made to determine if further purification of settlement inhibitor could be achieved by a stepwise elution of the C18 cartridge. Inhibitor was applied to the cartridge in distilled water, washed with 10 ml of distilled water and then eluted with 10 ml each of 10%, 30%, 50%, and 80% methanol. Settlement inhibitor eluted in the 80% fraction. Biological activity in the 80% eluate was comparable to that in the starting material. The recovery of solids in this fraction ranged from 6.3 to 1.0 µg/g of original homogenate.

TLC Separation of Inhibitor from L. virgulata

Microscope slide silica TLC plates were developed with 95% chloroform, and 5% methanol. The inhibitor fraction from the Sep-Pak$^R$ was separated into 8 quenching zones (visible under UV light) with R$_f$ values from 0.0 to 0.9. Only the zone with an R$_f$ of 0.65 to 0.75 was effective in inhibiting larval barnacle settlement. As shown later, this zone contained all four LV compounds identified in Table 1. Analytical reverse-phase TLC developed with 70% methanol yielded several zones with Rf values of 0 to 0.5. The zone with an R$_f$ of 0.34 inhibited settlement. This zone when chromatographed on silica in 95% chloroform, 5% methanol showed a single zone with an R$_f$ between 0.65 and 0.75.

Preparative Scale Purification of Settlement Inhibitor from L. virgulata

Procedures for obtaining settlement inhibitor were modified in order to decrease time taken to generate partially purified inhibitor and to increase the quantity of inhibitor obtained. The dialysis step and C$_{18}$ Sep-Pak$^R$ step were omitted and a methylene chloride extraction step and a preparative silica TLC step added. Analytical TLC on silica of material generated by the shortened extraction procedure showed an increase in organic contamination with three zones in the region of the original settlement inhibition activity. When assayed the combined zones had an of 2.6±1.0 mg ml$^{-1}$. The methylene chloride extracted material gave the same general pattern on preparative silica TLC plates as was observed with analytical TLC. Mobility of high R$_f$ zones was reduced approximately 10% on preparative plates. Two of the three zones in the inhibition region inhibited settlement. The most potent one, LVI had an EC$_{50}$ of 2.6±1.5 mg ml$^{-1}$. The other zone, LVII had an EC$_{50}$ of 12±5 mg ml$^{-1}$. On a dry weight basis the EC$_{50}$ of LVI was approximately 0.05 µg ml$^{-1}$, and LVII had an EC$_{50}$ of 0.20 µg ml$^{-1}$.

Affinity of Settlement Inhibitor from L. virgulata for Polystyrene and Glass Surfaces The behavior of settlement inhibitor on silica and reverse-phase TLC indicates that settlement inhibitor should have markedly different affinities for polystyrene and glass. In order to test the hypothesis that inhibitor acted by adsorbing to surfaces, a series of simultaneous parallel tests were conducted to determine the effective concentration for 50% inhibition of settlement upon glass and upon polystyrene surfaces. Glass is a substrate with relatively low affinity for inhibitor as evidenced by studies with Silica TLC plates. Polystyrene should have a high relative affinity because its adsorbtive characteristics are similar to the reverse-phase TLC material that showed relatively high affinity for inhibitor. Inhibitor was tested at concentrations 36, 18, 9, 4.5, 2.2, and 1.1 mg original $ml^{-1}$ to determine $EC_{50}$ of inhibitor for the two substrates. The $EC_{50}$ for glass was 12.9 (95% confidence, 15.4–9.9) and 11.7 (13.8–9.6) mg of al $ml^{-1}$ in separate determinations. Simultaneous determinations for polystyrene were $EC_{50}$ 7.4 (9.4–4.4) and 7.4 (9.4–4.4) mg original $ml^{-1}$ respectively. The $EC_{50}$ for inhibitor with polystyrene as the settlement substrate was significantly ($p<0.05$) lower than the $EC_{50}$ for glass.

Next, experiments determined if adsorption to surfaces was important for activity. The experiments included glass and polystyrene test containers and four treatments.

1. Control containers: seawater, cyprids and no other additions. Controls for treatments 3 and 4 were treated as were 3 and 4.
2. Settlement inhibitor: concentration series from 18 to 6 mg original $ml^{-1}$. These concentrations spanned the $EC_{50}$ confidence intervals of the inhibitor preparation on both substances.
3. The same inhibitor concentration series in #2 placed in containers for 5 min, then the inhibitor solution poured out, the containers rinsed and filled with fresh seawater.
4. Containers into which the inhibitor solution from #3 was poured.

For glass, settlement in controls was 85 to 89%. The inhibitor concentration series (#2) showed highly significant inhibition at all dilutions. The soaked, rinsed, seawater series (#3) showed statistical inhibition of settlement at rinse dilutions of 18 and 9 mg original $ml^{-1}$. At the most effective concentration settlement was >80% of control. The series receiving inhibitor solutions used for incubation of group 3 (#4) significantly inhibited settlement at all dilutions (Table 6). Settlement of group 4 was constantly lower than settlement of group 1.

TABLE 6

Absorption of inducer into glass.

| Treatment # | Treatment | Inhibitor Concen. | Number Tested | Percent Settled | G vs Cont | Sig |
|---|---|---|---|---|---|---|
| 1 | Control for 2 | 0 | 151 | 85 | — | — |
| 2 | Dilution series | 18 | 152 | 51 | 45 | <<.005 |
|   |   | 15 | 161 | 50 | 44 | <<.005 |
|   |   | 12 | 167 | 56 | 33 | <<.005 |
|   |   | 9 | 126 | 56 | 54 | <<.005 |
|   |   | 6 | 166 | 63 | 21 | <<.005 |
| 1 | Control for 3 | 0 | 209 | 88 | — | — |
| 3 | Rinsed with inhibitor solution | 18 | 128 | 73 | 11 | <.005 |
|   |   | 15 | 139 | 86 | 0.03 | NS |
|   |   | 12 | 147 | 88 | 0.01 | NS |
|   |   | 9 | 152 | 79 | 4.8 | <0.5 |
|   |   | 6 | 130 | 84 | 0.63 | NS |
| 1 | Control for 4 | 0 | 299 | 89 | — | — |
| 4 | Received inhibitor from 3 | 18 | 88 | 32 | 106 | <.005 |
|   |   | 15 | 95 | 38 | 92 | <.005 |
|   |   | 12 | 87 | 46 | 64 | <.005 |
|   |   | 9 | 120 | 47 | 80 | <.005 |
|   |   | 6 | 114 | 61 | 40 | <.005 |

For polystyrene, settlement in controls was 65 to 78%. The control inhibitor concentration series (2) showed significant inhibition at all dilutions. Dishes rinsed with inhibitor (group 3) inhibited settlement significantly at all dilutions, and the series receiving inhibitor solutions used for incubation of group 3 inhibited settlement at all solutions (Table 7). Group 2 was more inhibitory than either group 3 or group 4.

TABLE 7

Absorption of inducer onto polystyrene.

| Treatment # | Treatment | Inhibitor Concen. | Number Tested | Percent Settled | G vs Cont | Sig |
|---|---|---|---|---|---|---|
| 1 | concentration for 2 | 0 | 170 | 65 | — | — |
| 2 | dilution series | 18 | 192 | 15 | 101 | <.005 |
|   |   | 15 | 212 | 17 | 96 | <.005 |
|   |   | 12 | 102 | 15 | 69 | <.005 |
|   |   | 9 | 92 | 13 | 69 | <.005 |
|   |   | 6 | 42 | 17 | 32 | <.005 |
| 1 | concentration for 3 | 0 | 149 | 76 | — | — |
| 3 | rinsed with inhibitor solution | 18 | 229 | 48 | 28 | <.005 |
|   |   | 15 | 236 | 63 | 68 | <.005 |
|   |   | 12 | 94 | 42 | 27 | <.005 |
|   |   | 9 | 72 | 17 | 74 | <.005 |
|   |   | 6 | 62 | 39 | 25 | <.005 |
| 1 | concentration for 4 | 0 | 182 | 78 | — | — |
| 4 | received rinse from 3 | 18 | 205 | 25 | 110 | <.005 |
|   |   | 15 | 225 | 30 | 101 | <.005 |
|   |   | 12 | 89 | 26 | 59 | <.005 |
|   |   | 9 | 90 | 43 | 30 | <.005 |

TABLE 7-continued

| Absorption of inducer onto polystyrene. | | | | | |
|---|---|---|---|---|---|
| Treatment # | Treatment | Inhibitor Concen. | Number Tested | Percent Settled | G vs Cont | Sig |
| | | 6 | 77 | 30 | 52 | <.005 |

Comparison of the results of the adsorption experiments for the two substrates can be summarized as follows:
1. Settlement was higher in glass controls than in polystyrene controls.
2. Settlement was significantly inhibited for all dilutions tested in series #2 tests independent of surface. Settlement was lower on polystyrene than it was on glass.
3. The rinsed experimental series #3 showed rinsing polystyrene with inhibitor was more effective at inhibiting settlement than rinsing glass with inhibitor. Glass surfaces rinsed with inhibitor solutions were either not significantly inhibitory or inhibited settlement to about 80% of the control value. Every surface in the polystyrene series significantly inhibited settlement ($p<<0.005$). The least effective of the polystyrene series inhibited as effectively as the most effective of the glass treatment series. The remaining four treatments inhibited settlement to less than 65% of control values. The most effective treatment inhibited settlement to 22% of control values.
4. Sufficient inhibitor remained in the solutions that were used in rinsing surfaces in series #3 to inhibit settlement in all cases.

Settlement Inhibitor in Aqueous Homogenates of *Renilla reniformis*

Methanol extracts of two separate aqueous homogenates of *Renilla reniformis* were evaporated to dryness and tested in settlement assays at two-fold dilutions from 30 to 0.97 mg of original/ml. The most potent preparation inhibited settlement 100% except for the lowest concentration tested. Settlement in the 0.97 mg/ml solution was 9% of control. In the less potent preparation concentrations between 30 and 3.8 mg/ml inhibited settlement 100%. Settlement in the 1.87 mg/ml solution was 9% of control, and settlement in the 0.97 mg/ml solution was 25% of control. The $EC_{50}$ of both preparations was less than 0.70 mg/ml.

Methylene Chloride Extraction of *R. reniformis* Settlement Inhibitor Activity The methanol extracts tested above were fractionated by methylene chloride extraction. Dilution series assays tested the potencies of the aqueous methanol and methylene chloride extracts. The aqueous methanol fraction from the most potent preparation had significant ($p<0.03$) inhibitory activity at 100 and 22.5 mg/ml. Concentrations of 5.5 and 1.37 mg original ml$^{-1}$ facilitated settlement. The less potent preparation was significantly inhibitory at 100 mg original ml$^{-1}$ and had neither stimulatory or inhibitory activity at concentrations from 30 to 1.9 mg original ml$^{-1}$. Thus, most inhibitory activity was extracted from the aqueous methanol crude inhibitor preparation with methylene chloride.

The methylene chloride soluble material from the two preparations contained potent inhibitory activity. The least potent of the crude preparations was the source of the most potent methylene chloride soluble fraction. This preparation inhibited settlement to between 3 and 9% of the control level for concentrations between 20 and 2.5 mg/ml. Settlement at 1.25 mg/ml was 43% of control. The other preparation inhibited settlement 9–12% of control at 20 and 10 mg/ml and 27% of control at 5 mg/ml. Settlement at 2.5 mg/ml was at control levels.

Silica TLC Fractionation of Methylene Chloride Extracts of *R. reniformis* Containing Settlement Inhibitor Activity Methylene chloride extracts were fractionated by thin layer chromatography on silica. Development of the methylene chloride fraction of inhibitor on silica with 9:1 methylene chloride:acetonitrile yielded several UV quenching regions with relative mobilities ranging from 0.0 to 0.9. Settlement inhibition was localized in the regions with relative mobilities between 0.2 and 0.55 (Table 2, FIG. 1). Later studies showed three active bands (UV quenching) on standard silica plates with $R_f$ values of ca 0.4–0.5, 0.3–0.4 and 0.25–0.3. There were occasional inconsistencies in Rf but the bands appeared to maintain the same Rf relationship. In some preparations, the slowest band was missing or very weak.

$EC_{50}$ values of <0.8 to 9 mg original animal ml$^{-1}$ were obtained on eluates of these bands (Table 3).

Reverse-Phase TLC Fractionation of Settlement Inhibitors from Renilla reniformis Using the best system of acetonitrile:water 2:1 in Whatman PKLC18F plates, additional fractionation of the materials from normal silica TLC could be obtained.

Figure 2:
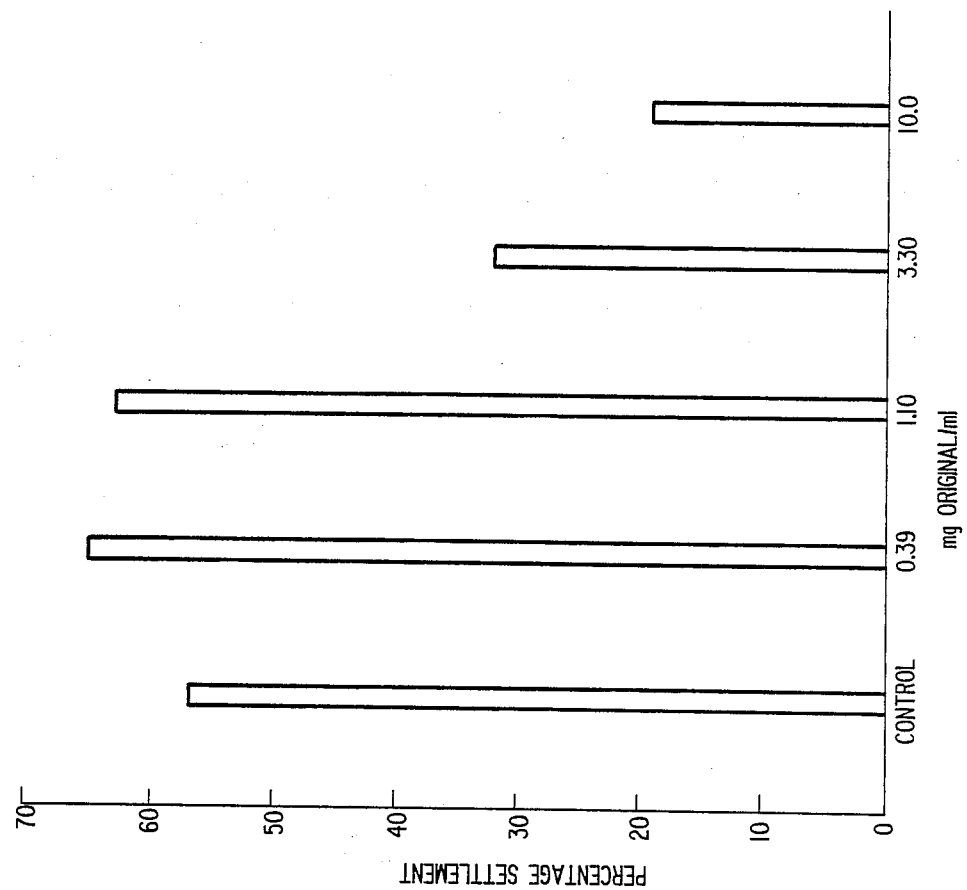
FIG. 2 is a graph showing a dilution series assay of reverse-phase band $R_f=0.42-0.5$. This band contained relatively weak antisettlement activity.
Figure 3:
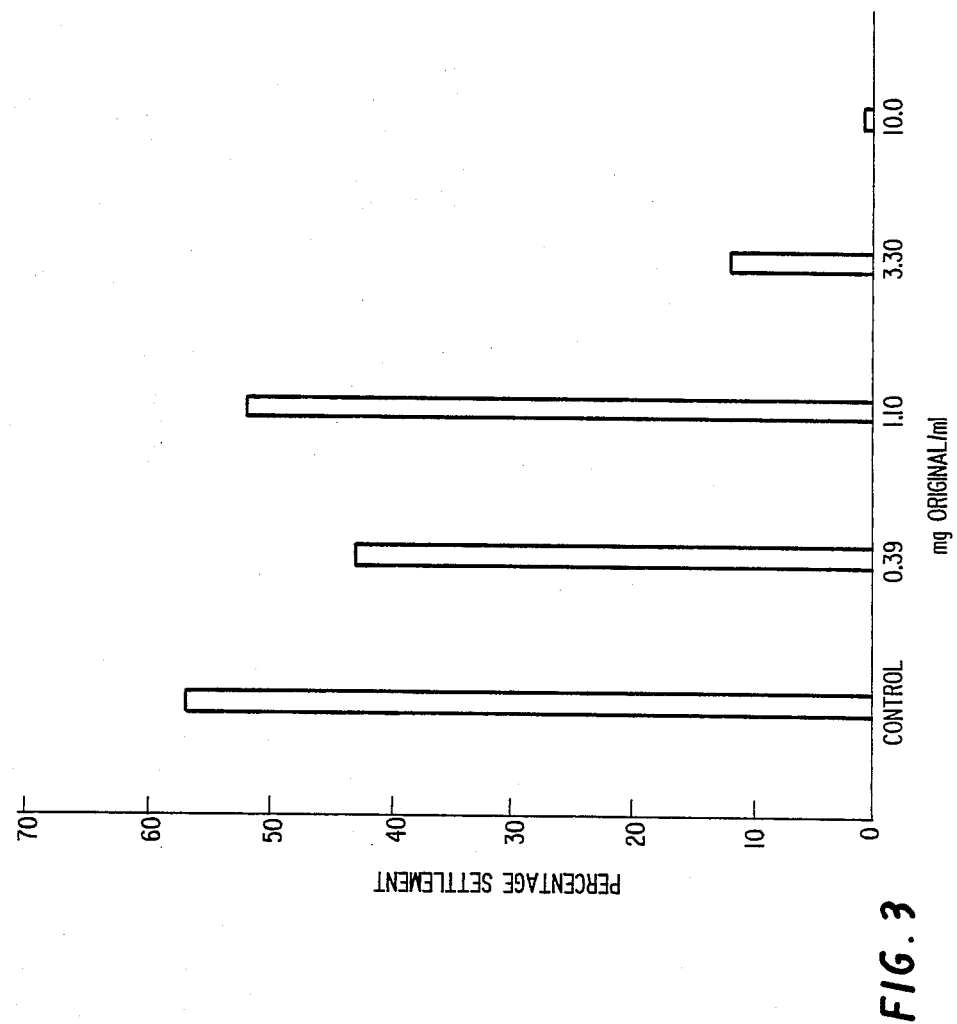
FIG. 3 is a graph showing a dilution series assay of silica band $R_f=0.50-0.60$. This band contained relatively strong antisettlement activity. Nearly complete settlement inhibition was observed at 10 mg original ml$^{-1}$.
Figure 4:
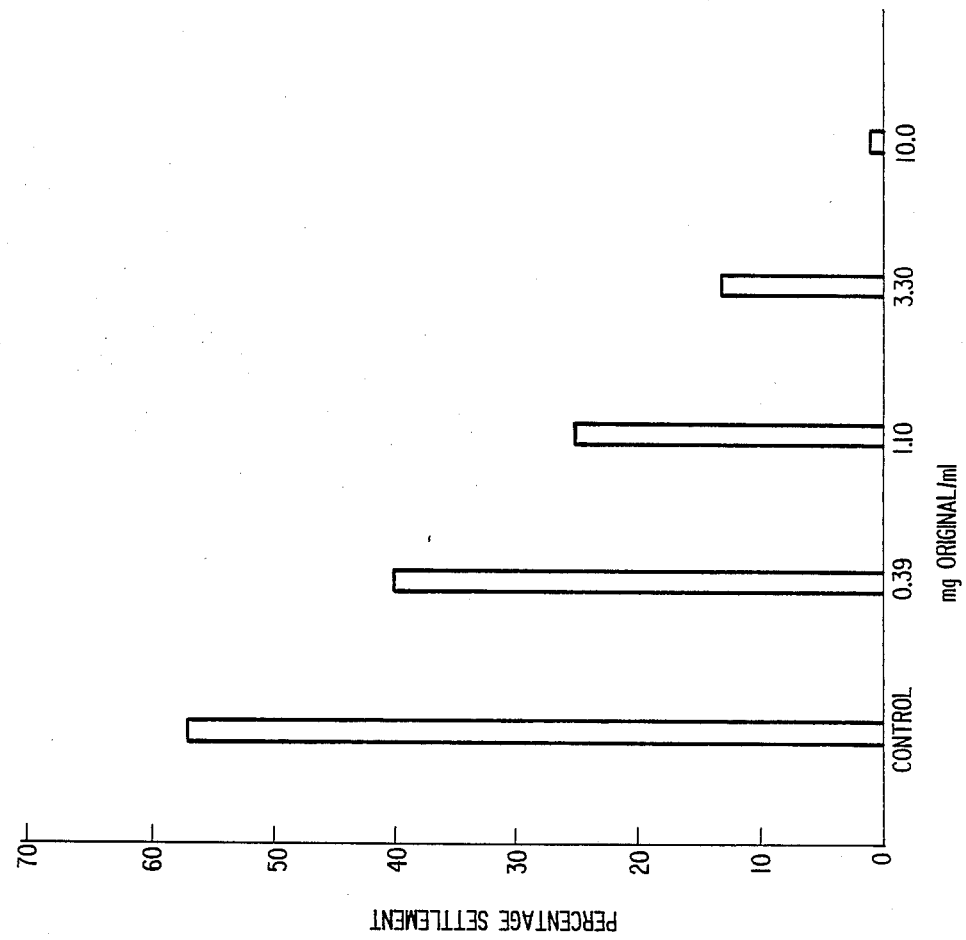
FIG. 4 is a graph showing a dilution series assay of reverse-phase band $R_f=0.60-0.65$. This band contained strong antisettlement activity. Nearly complete settlement inhibition was observed at 10 mg original ml$^{-1}$. Significant settlement inhibition was observed at 0.39 mg original ml$^{-1}$, the lowest concentration tested.

The silica TLC band of $R_f$ 0.4–0.5 gave a reverse phase partition three bands with $R_f$'s of ca 0.6–0.65, 0.5–0.6, and 0.42–0.5. All were active in the settlement assay (FIGS. 2–4).

The material with $R_f$ on silica of 0.3–0.4 gives one main active band in reverse phase TLC, $R_f$ 0.55–0.65 and a faster running minor band which appears to be inactive. Further characterization of these materials is underway.

TABLE 8

Mobilities and effective concentrations of barnacle settlement inhibitors chromatographed on silica. Methylene chloride extract was developed with 9:1 methylene chloride:acetonitrile.

| Mobility Relative to Front | $EC_{50}$ mg Original per ml | 95% Confidence Interval |
|---|---|---|
| 0.39 | 5.5 | 7.5–3.3 |
| 0.46 | 1.0 | 1.3–0.6 |
| 0.53 | 2.1 | 2.7–1.4 |

TABLE 9

Mobilities and effective concentrations of
barnacle settlement inhibitors
chromatographed on $C_{18}$ silica. The active
zone (all three regions from Table 1) was
applied to reversed phase silica and
developed with 3:1 acetonitrile:water.

| Mobility Relative to Front | $EC_{50}$ mg Original per ml | 95% Confidence Interval |
| --- | --- | --- |
| 0.49 | 0.8 | 1.7–0.0 |
| 0.54 | 4.8 | 5.8–4.0 |
| 0.62 | 9.0 | 10.7–6.8 |

All publications identified specifically in this application are indications of the knowledge of those skilled in the art at the time this invention was made. Each reference is accordingly herein incorporated by reference individually at the location where cited as if incorporation by reference were specifically mentioned at that location.

The invention now being fully described, it will be recognized by one of ordinary skill in the art that many changes and modifications can be made thereto without departing from the spirit or scope of the invention as set forth herein.

What is claimed as new and desired to be secured by Letters Patent of the United States is:

1. A compound of the formula

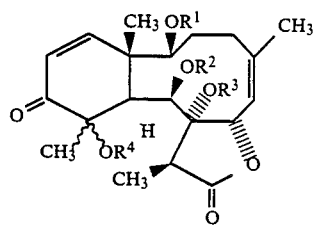

in which $R^1$-$R^4$ independently represent H or a $C_{1-18}$ alkanoyl or alkenoyl group.

2. The compound of claim 1, wherein $R^3$ and $R^4$ are both H.

3. The compound of claim 1, wherein $R^1$ and $R^2$ are acetate.

4. The compound of claim 1, wherein one of $R^1$ and $R^2$ is acetate and the other is propionate.

5. The compound of claim 1, wherein one of $R^1$ and $R^2$ is acetate and the other is butyrate.

6. A method of inhibiting barnacle settlement which comprises applying a composition containing a compound of the formula

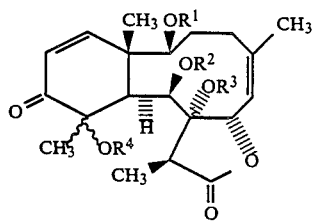

in which $R^1$-$R^4$ independently represent H or a $C_{1-18}$ alkanoyl or alkenoyl group to an aquatic surface.

7. The method of claim 6, wherein said composition is a paint.

* * * * *